(12) United States Patent
Utturkar et al.

(10) Patent No.: US 11,491,049 B2
(45) Date of Patent: Nov. 8, 2022

(54) BODY PHYSIOLOGICAL PARAMETER DETERMINING

(71) Applicant: GENERAL ELECTRIC COMPANY, Schenectady, NY (US)

(72) Inventors: Yogen Vishwas Utturkar, Niskayuna, NY (US); Ernst Wolfgang Stautner, Niskayuna, NY (US); Pradeep Salapakkam, Mason, OH (US); Bryan Whalen, Gansevoort, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1579 days.

(21) Appl. No.: 14/961,316

(22) Filed: Dec. 7, 2015

(65) Prior Publication Data

US 2017/0156923 A1 Jun. 8, 2017

(51) Int. Cl.
*A61F 7/00* (2006.01)
*H05B 1/02* (2006.01)
*H05B 3/00* (2006.01)
*A61B 5/01* (2006.01)
(Continued)

(52) U.S. Cl.
CPC ............... *A61F 7/007* (2013.01); *A61B 5/01* (2013.01); *A61B 5/4836* (2013.01); *A61B 5/7278* (2013.01); *H05B 1/0202* (2013.01); *H05B 1/025* (2013.01); *H05B 3/0014* (2013.01); *A61B 2503/045* (2013.01); *A61B 2560/0242* (2013.01); *A61B 2560/0252* (2013.01); *A61F 2007/0071* (2013.01); *A61F 2007/0088* (2013.01); *A61G 11/00* (2013.01); *A61G 2203/46* (2013.01); *A61G 2210/90* (2013.01)

(58) Field of Classification Search
CPC .............. A61F 7/007; A61F 2007/0071; A61F 2007/0088; A61B 5/4836; A61B 5/7278; A61B 5/01; A61B 2560/0252; A61B 2503/045; A61B 2560/0242; A61G 2203/46; A61G 2210/90; A61G 11/00
See application file for complete search history.

(56) References Cited

U.S. PATENT DOCUMENTS 5,073,688 A    12/1991  McCormack
5,119,467 A *   6/1992  Barsky .................... H05B 3/26
                                                   338/308
(Continued)

FOREIGN PATENT DOCUMENTS

DE      102013007631 A1    11/2014
WO         2015092627 A1     6/2015

OTHER PUBLICATIONS

International Search Report and Written Opinion issued in connection with corresponding Application No. PCT/US2016/055481 dated Dec. 8, 2016.

(Continued)

*Primary Examiner* — Kaitlyn E Smith
*Assistant Examiner* — Yasmin Ekrami
(74) *Attorney, Agent, or Firm* — Andrus Intellectual Property Law, LLP

(57) ABSTRACT

Methods systems and apparatus are set forth herein. There is provided in one embodiment determining one or more body physiological parameter of a patient based on one or more input; and controlling a heating system for warming the patient based on a result of the determining.

30 Claims, 7 Drawing Sheets

(51) Int. Cl.
*A61B 5/00* (2006.01)
*A61G 11/00* (2006.01)

(56) References Cited

U.S. PATENT DOCUMENTS

| | | | |
|---|---|---|---|
| 5,291,748 A * | 3/1994 | Ueda | B60H 1/00742 |
| | | | 236/78 D |
| 5,415,618 A * | 5/1995 | Koch | A61G 11/00 |
| | | | 600/22 |
| 6,048,304 A * | 4/2000 | Koch | G05D 23/1931 |
| | | | 600/22 |
| 6,464,627 B1 | 10/2002 | Falk | |
| 6,692,518 B2 | 2/2004 | Carson | |
| 9,320,642 B1 * | 4/2016 | Van Oudenallen | A61B 34/10 |
| 2002/0147381 A1 * | 10/2002 | Kolarovic | A61G 11/00 |
| | | | 600/22 |
| 2005/0215844 A1 * | 9/2005 | Ten Eyck | A61B 5/02055 |
| | | | 600/22 |
| 2005/0284470 A1 * | 12/2005 | Wei | A61M 16/107 |
| | | | 128/200.14 |
| 2006/0122673 A1 | 6/2006 | Callister | |
| 2007/0086506 A1 | 4/2007 | Dicks et al. | |
| 2012/0235633 A1 * | 9/2012 | Kesler | H03H 7/40 |
| | | | 320/108 |
| 2012/0310439 A1 * | 12/2012 | Lin | G05D 23/19 |
| | | | 700/300 |
| 2013/0255930 A1 | 10/2013 | Prakah-Asante | |
| 2013/0340770 A1 | 12/2013 | Starr et al. | |
| 2014/0142462 A1 | 5/2014 | Fazzi et al. | |
| 2014/0303694 A1 * | 10/2014 | Timme | A61M 16/024 |
| | | | 607/96 |
| 2015/0057963 A1 | 2/2015 | Zakharov et al. | |
| 2015/0182406 A1 * | 7/2015 | Falk | A61G 11/00 |
| | | | 600/22 |
| 2015/0204561 A1 * | 7/2015 | Sadwick | F24F 11/30 |
| | | | 236/1 C |
| 2015/0272802 A1 * | 10/2015 | Tsitlik | A61G 11/00 |
| | | | 600/301 |
| 2016/0015927 A1 * | 1/2016 | Winski | A61M 16/16 |
| | | | 128/203.14 |
| 2016/0081629 A1 * | 3/2016 | Rostalski | A61B 5/01 |
| | | | 600/549 |
| 2016/0206493 A1 * | 7/2016 | Rapoport | A61G 11/00 |

OTHER PUBLICATIONS

A.P. Gagge; "Standard Operative Temperature, a Single Measure of the Combined Effect of Radiant Temperature, of Ambient Air Temperature and of Air Movement of the Human Body," Temperature Its Measurement and Control in Science and Industry Symposium, American Institute of Physics, Nov. 1939, pp. 544-552, New York City.
A.P. Gagge: "A New Physiological Variable Associated with Sensible and Insensible Perspiration," Apr. 3, 1937, pp. 277-287.
Molgat-Seon, et al; "Accidental overheating of a newborn under an infant radiant warmer: a lesson for future use," Journal of Perinatology, 2013, vol. 33, pp. 738-739.
Neonatal Incubator/Infant Radiant Warmer—Ohmeda Giraffe OmniBed, MDA Evaluation 02090, Jul. 2002.
TINC 101 Transport Incubator from Phoenix web page, <http://www.news-medical.net/TINC-101-Transport-Incubator-from-Phoenix>, 2 pages, Jan. 20, 2013, retrieved from Internet Archive <http://web.archive.org/web/20130120213918/http://www.news-medical.net/TINC-101-Transport-Incubator-from-Phoenix> on Dec. 7, 2015.
Fraguela, et al; "Mathematical modelling of thermoregulation processes for premature infants in closed convectively heated incubators," Computers in Biology and Medicine, Feb. 1, 2015, pp. 159-172, vol. 57.

* cited by examiner

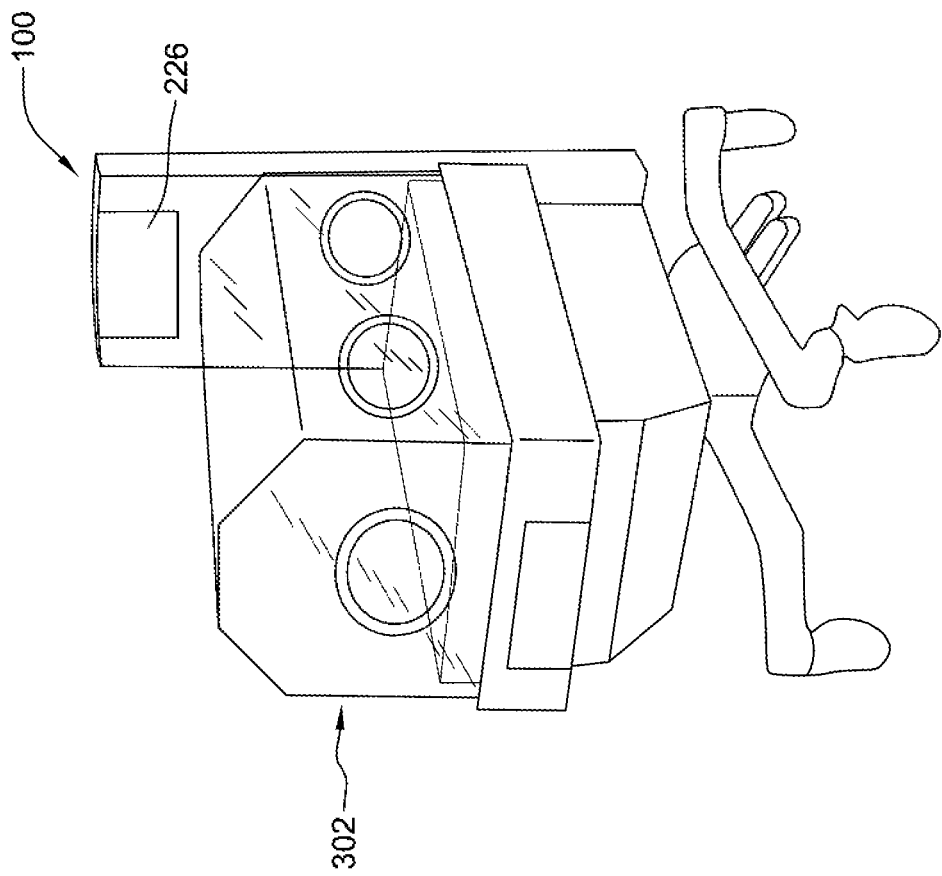
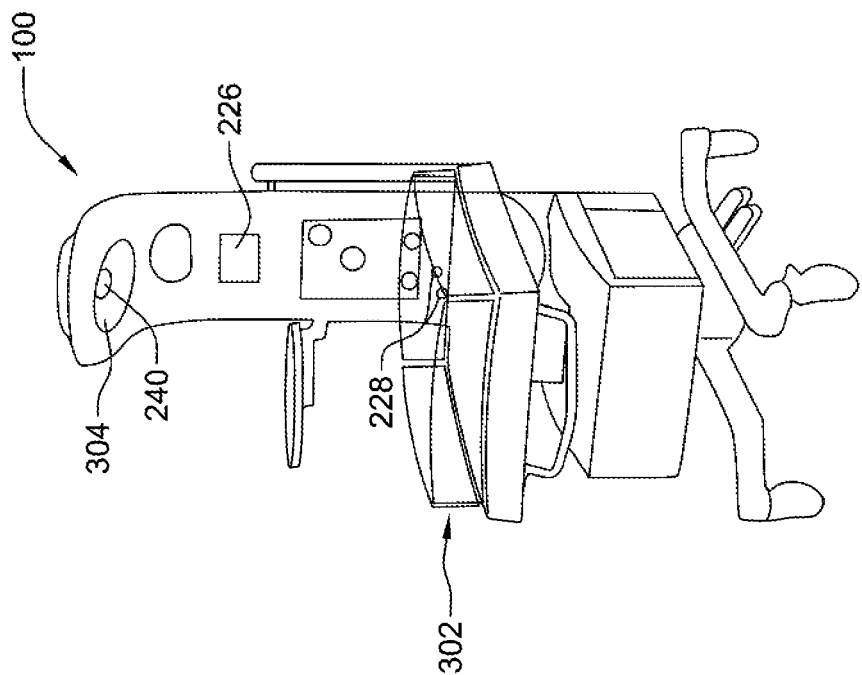

TYPICAL CASE
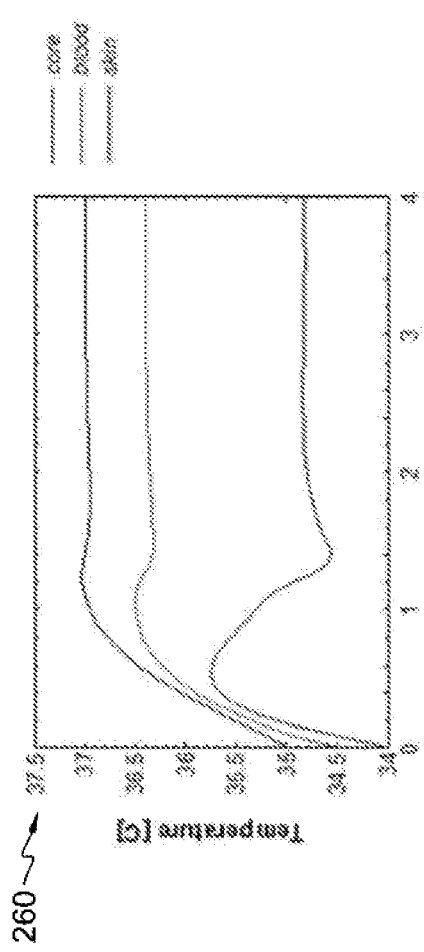
FIG. 6D
FIG. 6E
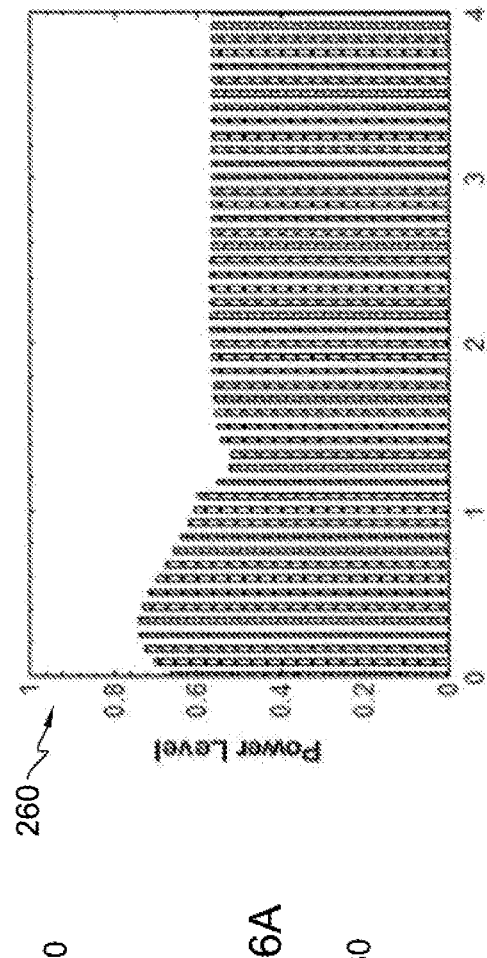
FIG. 6A
FIG. 6B
FIG. 6C

HIGH CIRCULATION RATE CASE
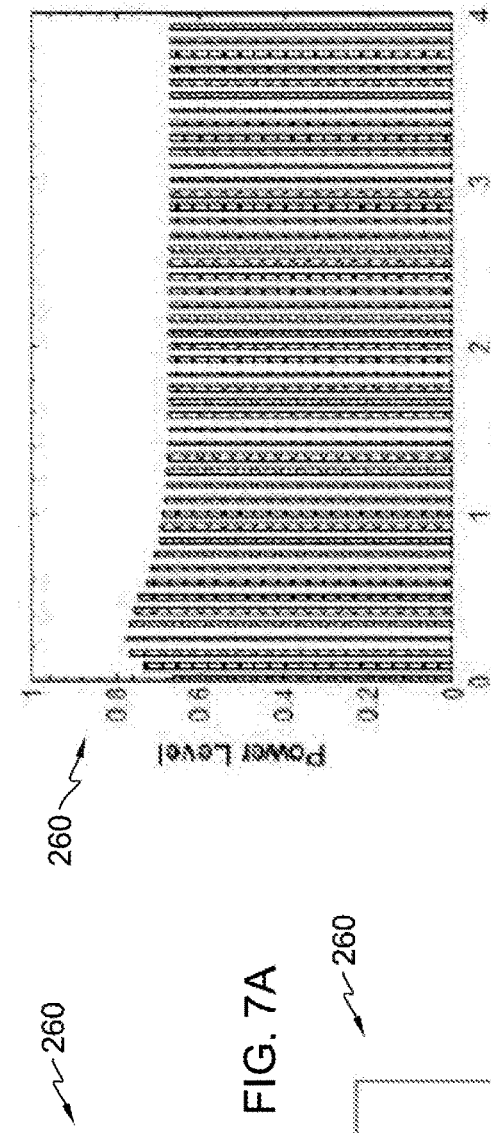
FIG. 7A
FIG. 7B
FIG. 7C
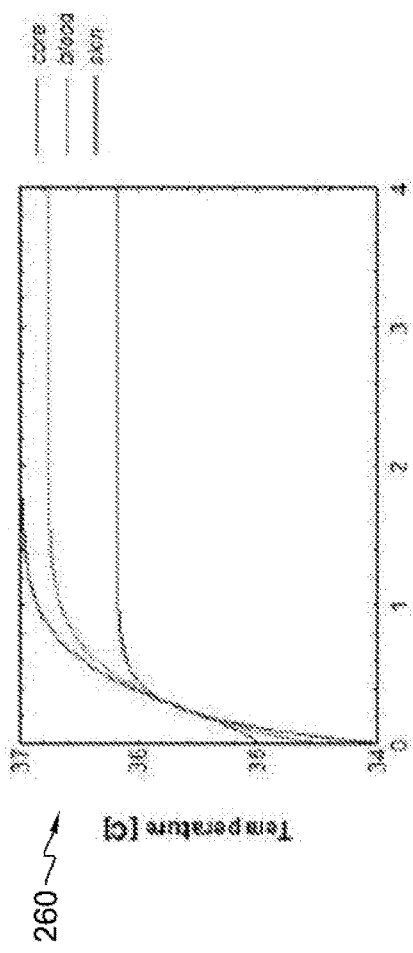
FIG. 7D
FIG. 7E

QUIESCENT ROOM CONDITIONS CASE
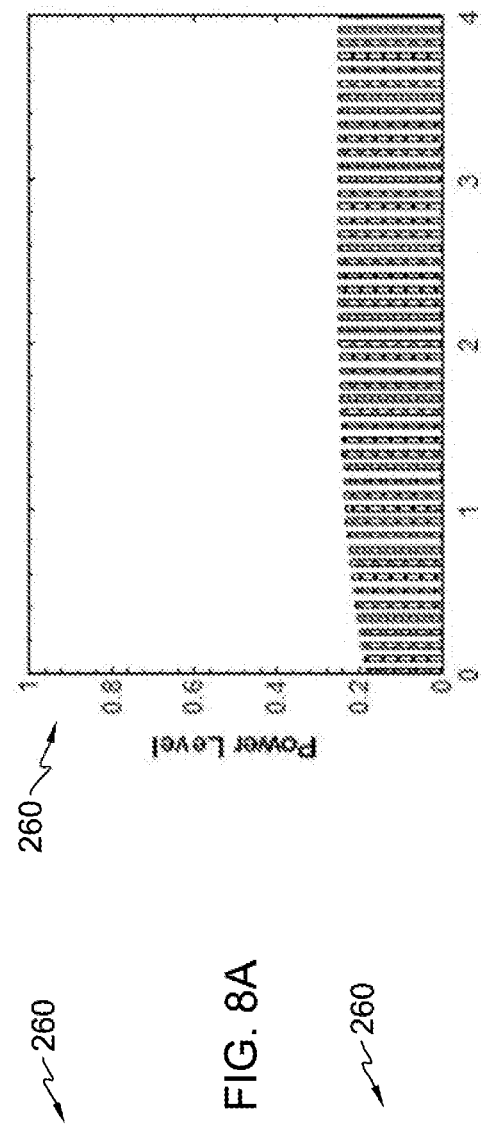
FIG. 8A
FIG. 8B
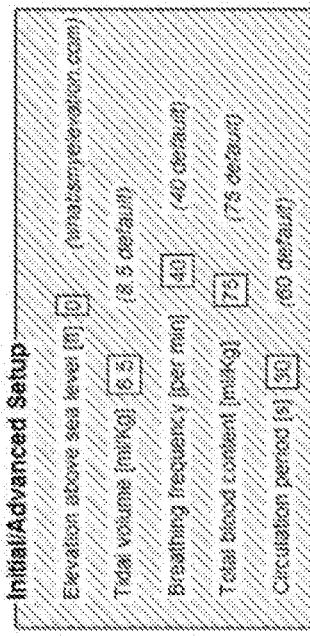
FIG. 8C
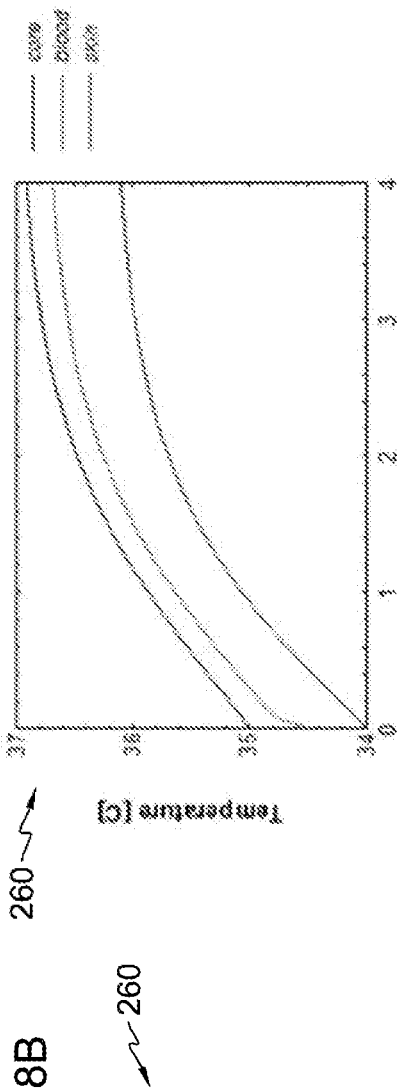
FIG. 8D
FIG. 8E

BODY PHYSIOLOGICAL PARAMETER DETERMINING

The disclosure relates to parameter determination in general and in particular to body physiological parameter determining.

BACKGROUND

Body temperature is one of the four main vital signs that must be monitored to ensure safe and effective care. Temperature measurement is recommended by the National Institute of Clinical Excellence a part of the initial assessment in acute illness in adults (NICE, 2007), and is regarded as an important clinical measurement in all patients of any age including infants. Despite applying in all healthcare environments, wide variations exist on the methods and techniques used to measure body temperature.

BRIEF DESCRIPTION

Methods systems and apparatus are set forth herein. There is provided in one embodiment determining one or more body physiological parameter of a patient based on one or more input; and controlling a heating system for warming the patient based on a result of the determining.

DRAWINGS

FIG. 3 is a perspective physical form view of an apparatus according to one embodiment;

FIG. 4 is perspective physical form view of an apparatus according to one embodiment;

FIGS. 6A-6E, 7A-7E, and 8A-8E are screen displays illustrating various illustrative use cases.

DETAILED DESCRIPTION

Figure 1:
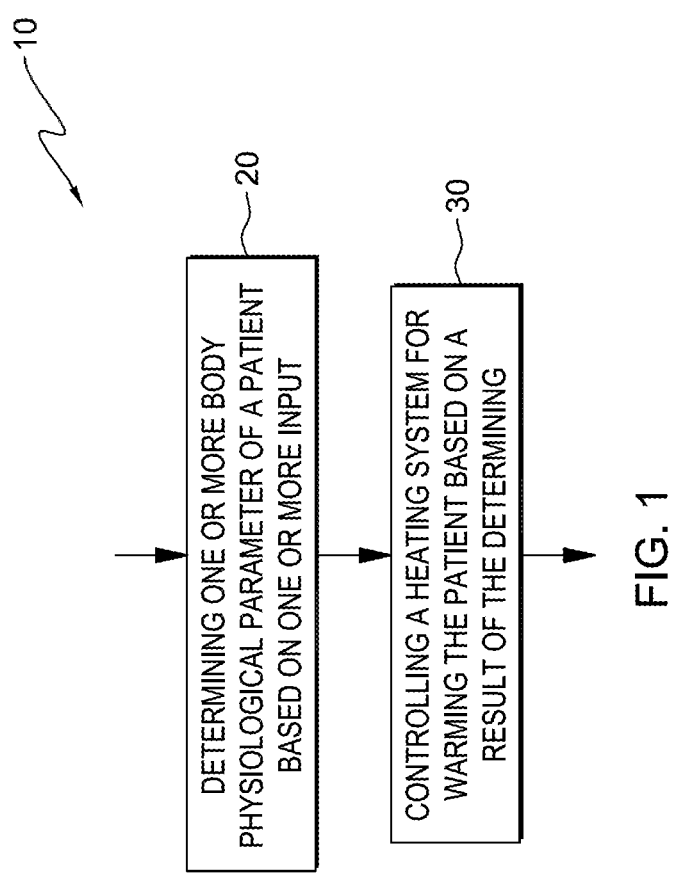
FIG. 1 is a flow diagram illustrating a method according to one embodiment.

A method 10 referred to in FIG. 1 can include at block 20 determining one or more body temperature parameter of a patient based on one or more input; and at block 30 can include controlling a heating system for warming the patient based on a result of the determining.

In one embodiment, the one or more body temperature parameter can be provided by, e.g., body core temperature, a blood temperature and/or a body skin temperature.

In one embodiment, the determining one or more body temperature parameter can include determining one or more body temperature parameter over time. A body temperature can be e.g. a body core temperature, a blood temperature, or a skin temperature.

In one embodiment, the determining can include using one or more heat balance function that defines a body temperature parameter over time.

In one embodiment, the one or more body temperature parameter can include a body core temperature and the controlling can include controlling the heating system to maintain the body core temperature to a setpoint.

In one embodiment, the one or more input can be a one time obtained input. In one embodiment the one or more input can be a repetitively obtained input. In one embodiment, the one or more input can be a sensor input obtained from a sensor. In one embodiment the one or more input can be a characterizing input that is not a sensor input. In one embodiment the one or more input can be an online input obtained without operator entry. In one embodiment the one or more input can be an operator entered input obtained based on operator entry. In one embodiment the one or more input can be a physiological sensor input obtained from a physiological sensor. In one embodiment the one or more input can be an environmental sensor input obtained from an environmental sensor.

In one embodiment, a method as set forth herein can determine a current body temperature parameter, e.g., core temperature, blood temperature, skin temperature, without performing a current measurement of a current body temperature parameter. As such, a method herein can avoid a body temperature measurement process that can be uncomfortable or even harmful to patient under care. While one possible use envisions body temperature parameter determining for infants, methods herein have wide applicability.

In one embodiment, a method as set forth herein can determine a current core temperature without performing a current measurement of current core temperature. As such a method herein can avoid a core temperature measurement process that can be uncomfortable or even harmful to patient under care. While one possible use envisions infants, methods herein have wide applicability.

Figure 2:
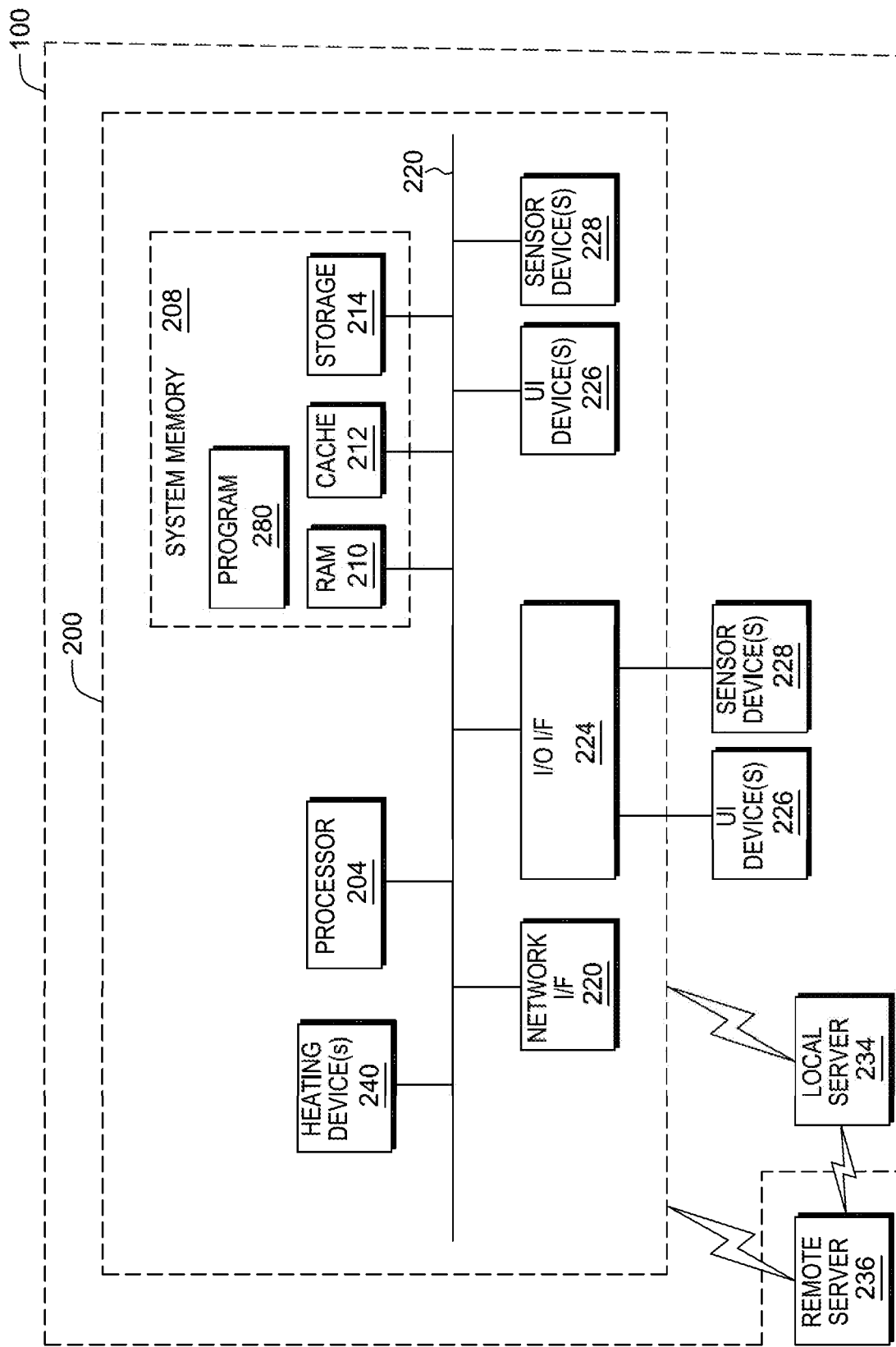
FIG. 2 is a block diagram of an apparatus according to one embodiment.

In one embodiment, a method as set forth herein can be performed with use of an apparatus 100 as shown in FIG. 2 having a signal processing circuit 200. In one embodiment a signal processing circuit 200 can be processor based. As shown in FIG. 2, processing circuit 200 of apparatus 100 is shown in the form of a general-purpose computing device. In one embodiment, the components of signal processing circuit 200 may include, e.g., one or more processor 204, a system memory 208, and a bus 220. Bus 220 can couple various system components including system memory 208 to one or more processor 204.

In one embodiment, system memory 208 can include computer system readable media in the form of volatile memory, such as random access memory (RAM) 210 and/or cache memory 212. System memory 208 of signal processing circuit 200 may further include other removable/non-removable, volatile/non-volatile computer system storage media. By way of example only, storage system 214 can be provided for reading from and writing to a non-removable, non-volatile magnetic media. Storage system 214 can be provided, e.g., by a hard drive. One or more program 280 for performing of methods herein can be stored in system memory 208.

Signal processing circuit 200 may also communicate with one or more external user interface device 226 such as a keyboard, a pointing device, a display (e.g., with or without touch screen) etc. that enable a user to interact with signal processing circuit 200; and/or any devices (e.g., network card, modem, etc.) that enable signal processing circuit 200 to communicate with one or more other signal processing circuit 200 configured generally in the manner of signal processing circuit 200; and/or one or more sensor 228. Such communication can occur via one or more Input/Output (I/O) interface 224. In one embodiment, an external user interface device 226 can be provided by a display of a mobile device, e.g., laptop, mobile phone, tablet, in communication with signal processing circuit 200.

Signal processing circuit 200 can communicate with one or more network such as a local area network (LAN), a general wide area network (WAN), and/or a public network (e.g., the Internet) via network communication interface 230. As depicted, network communication interface 230 can communicate with the other components of signal processing circuit 200 via bus 220. Via one or more I/O interface 224 and/or network communication interface 230 signal processing circuit 200 can be in communication with external local server 234 and/or remote server 236.

In addition to or in place of having one or more external user interface device 226 which can be configured to provide user interface functionality, apparatus 100 in one embodiment can include one or more internal user interface device 226 connected to bus 220. In one embodiment, user interface device 226 connected to bus 220 can be configured as a touch screen display and can be configured to provide user interface functionality. Signal processing circuit 200 in one embodiment can also include one or more sensor 228 connected to bus 18. One or more sensor 228 can alternatively be connected through I/O interface(s) 224.

In one embodiment, one or more sensor 228 can be provided, e.g., by a patient physiological sensor, e.g., a skin temperature sensor, a blood temperature sensor, a breathing rate sensor, a tidal breathing airflow sensor, a blood volume sensor, weight sensor, and/or a heart rate sensor. A tidal breathing airflow sensor can detect shifts in breathing patterns, volume and frequency and can be attached on a patient's nose. In one embodiment, one or more sensor 228 can be provided, e.g., by an environmental sensor, e.g., an air temperature sensor, an air velocity sensor, an air humidity sensor. These sensors can either be supported on or adjacent to the patient's body (typically in the case of a physiological sensor) or the apparatus itself (typically in the case of an environmental sensor). In one embodiment, at least one sensor of one or more sensor 228 can provide data continuously at a predetermined frequency. In one embodiment, at least one sensor of one or more sensor 228 can provide data on a one time basis. In one embodiment, wherein one or more sensor 228 is provided by a weight sensor a weight value may not be provided repetitively because the shifts are slower compared to the other variables (depending on baby's growth). In one embodiment, weight values can either be pre-measured on a separate weight scale or through a scale integrated within a patient bed of apparatus 100. In one embodiment, where a sensor herein repetitively provides data, one or more program 280 may obtain the data as an input at the times that the data is provided. In one embodiment, where a sensor herein repetitively provides data, one or more program 280 may obtain the data as an input at times other than times at which the data is provided.

In one embodiment, one or more sensor 228 can be provided, e.g., an air temperature sensor. The air temperature sensor can provide a value for the air temperature. In one embodiment, one or more sensor 228 can be provided, e.g., an air velocity sensor. The air velocity sensor can provide a value for air local velocity.

Signal processing circuit 200 can also include one or more heating device 240 connected to system bus 220. One or more heating device 240 can define a heating system for providing heat.

One or more program 280 can generally carry out the functions and/or methodologies of embodiments as described herein. One or more program 280 can include computer readable program instructions that can be stored in a computer readable storage medium within a respective computing device. In one embodiment a computer readable storage medium as set forth herein can be included in a system memory 208 as set forth in FIG. 2.

There can be provided herein, a method, and/or a computer program product at any possible technical detail level of integration. The computer program product may include a computer readable storage medium (or media) having computer readable program instructions thereon for causing one or more processor to carry out aspects as set forth herein.

The computer readable storage medium can be a tangible device that can store instructions for use by an instruction execution device. The computer readable storage medium may be, for example, but is not limited to, an electronic storage device, a magnetic storage device, an optical storage device, an electromagnetic storage device, a semiconductor storage device. The computer readable storage medium can be provided by any suitable combination of the foregoing. A computer readable storage medium can be provided by, e.g., a portable computer diskette, a hard disk, a random access memory (RAM), a static random access memory (SRAM), a read-only memory (ROM), an erasable programmable read-only memory (EPROM or Flash memory), a digital versatile disk (DVD), a portable compact disc read-only memory (CD-ROM), Physical form views of apparatus 100 in various embodiments are set forth herein in reference to FIGS. 3 and 4. While methods and apparatus herein have widespread use one particular use is for determining a body physiological parameter of an infant. In FIG. 3, apparatus 100 is shown as being provided by an infant temperature control apparatus provided by a baby warmer having an open baby holding area. In FIG. 4, apparatus 100 is shown as being provided by an infant temperature control apparatus provided by an incubator having a closed baby holding area. While apparatus 100 can be adapted for use with infants it can be seen that an apparatus 100 for providing temperature control can be scaled to any size for use with any size patient. Further, apparatus 100 need not be a mobile apparatus as shown in FIGS. 3 and 4 but may be, e.g., partially or fully integrated in a building infrastructure.

In one embodiment, the method 10 as shown in FIG. 1 can be performed using one or more program 280 running on one or more processor 204 of signal processing circuit 200. At block 20 one or more program 280 can perform determining one or more body physiological parameter of a patient based on one or more input and at block 30 one or more program 280 can perform controlling a heating system for warming the patient based on a result of the determining.

In one embodiment, one or more program 280 can solve one or more heat balance equation for performing determining of one or more body physiological parameter at block 20. Examples of heat balance equations that can be solved include the following heat balance equations.

$$\text{Heat\_gain}_{core} - \text{Heat\_loss}_{core} = \text{Change of core heat capacity} = \text{Mass}_{core} \times \text{specific\_heat\_capacity}_{core} \times d/dt \, (\text{temperature}_{core}) \quad \text{(Eq. 1)}$$

$$\text{Heat\_gain}_{blood} - \text{Heat\_loss}_{blood} = \text{Change of core heat capacity} = \text{Mass}_{blood} \times \text{specific\_heat\_capacity}_{blood} \times d/dt \, (\text{temperature}_{blood}) \quad \text{(Eq. 2)}$$

$$\text{Heat\_gain}_{skin} - \text{Heat\_loss}_{skin} = \text{Change of skin heat capacity} = \text{Mass}_{skin} \times \text{specific\_heat\_capacity}_{skin} \times d/dt \, (\text{temperature}_{skin}) \quad \text{(Eq. 3)}$$

In one or more program 280 at block 20 can solve one or more of the heat balance equations Eq. 1 Eq. 2 Eq. 3 for determining one or more body temperature parameter over time.

Regarding Eq. 1. the parameter Heat_gain$_{core}$ can be expressed as a function of metabolism, e.g., Metabolism of Brown Adiposed Fats, e.g., $$\text{Heat\_gain}_{core} = \text{Metabolism of Brown Adipose Fats} \quad \text{(Eq. 4)}$$

In one embodiment, Metabolism of Brown Adipose Fats can be expressed as a function of parameters, e.g., $$\text{Metabolism of Brown Adipose Fats} = f(\text{rate of oxygen consumption, oxygen/CO}_2 \text{ ratio in respiration}) \quad \text{(Eq. 5)}$$

Regarding Eq. 1. the component Heat_loss$_{core}$ can be expressed as a function of Heat transport to blood and heat loss though respiration, e.g., $$\text{Heat\_loss}_{core} = \text{Heat transport to blood} + \text{Heat loss through respiration} \quad \text{(Eq. 6)}$$

In one embodiment, Heat transport to blood can be expressed as a function of parameters, e.g., $$\text{Heat transport to blood} = f(\text{temperature}_{blood}, \text{heart rate, total blood content}) \quad \text{(Eq. 7)}$$

In one embodiment, Heat loss through respiration can be expressed as a function of parameters, e.g., $$\text{Heat loss through respiration} = f(\text{respiratory rate, lung tidal volume, exhaled air temperature, air temperature, humidity}) \quad \text{(Eq. 8)}$$

Regarding Eq. 2. the parameter Heat_gain$_{blood}$ can be expressed as a function of Heat transport from the core, e.g., $$\text{Heat\_gain}_{blood} = \text{Heat transport from the core} \quad \text{(Eq. 9)}$$

In one embodiment, Heat transport from the core can be expressed as a function of parameters, e.g., $$\text{Heat transport from the core} = f(\text{temperature}_{core}, \text{heart rate, total blood content}) \quad \text{(Eq. 10)}$$

Regarding Eq. 2. the component Heat_loss$_{blood}$ can be expressed as a function of Heat transport to the skin, e.g., $$\text{Heat\_loss}_{blood} = \text{Heat transport to the skin} \quad \text{(Eq. 11)}$$

In one embodiment, Heat transport to the skin can be expressed as a function of parameters, e.g., $$\text{Heat transport to the skin} = f(\text{temperature}_{skin}, \text{heart rate, total blood content}) \quad \text{(Eq. 12)}$$

Regarding Eq. 3. the parameter Heat_gain$_{skin}$ can be expressed as a function of Heat from a radiant warmer and Heat transport from the blood, e.g., $$\text{Heat\_gain}_{skin} = \text{Heat from Radiant Warmer} + \text{Heat transport from the blood} \quad \text{(Eq. 13)}$$

In one embodiment, Heat from Radiant Warmer can be expressed as a function of parameters, e.g., $$\text{Heat from Radiant Warmer} = f(\text{heating system power level, view factor between heating system and patient}) \quad \text{(Eq. 14)}$$

In one embodiment, Heat transport from the blood can be expressed as a function of parameters, e.g., $$\text{Heat transport from the blood} = f(\text{oxygen consumption rate, oxygen/CO}_2 \text{ ratio in respiration}) \quad \text{(Eq. 15)}$$

Regarding Eq. 3. the parameter Heat_loss$_{skin}$ can be expressed as a function of Heat loss to a mattress, heat loss to air currents, Radiation heat loss, and skin water loss, e.g., $$\text{Heat\_loss}_{skin} = \text{Heat loss to mattress} + \text{Heat loss to air currents} + \text{Radiation heat loss} + \text{skin water loss} \quad \text{(Eq. 16)}$$

In one embodiment, Heat loss to a mattress can be expressed as a function of parameters, e.g., $$\text{Heat loss to a mattress} = f(\text{mattress temperature, mattress conductivity, fraction of skin in contact with mattress}) \quad \text{(Eq. 17)}$$

In one embodiment, heat loss to air currents can be expressed as a function of parameters, e.g., $$\text{Heat loss to air currents} = f(\text{air temperature, air speed, fraction of skin exposed to air}) \quad \text{(Eq. 18)}$$

In one embodiment, Radiation heat loss can be expressed as a function of parameters, e.g., $$\text{Radiation heat loss} = f(\text{temperature}_{walls}, \text{view factor between patient and walls}) \quad \text{(Eq. 19)}$$

In one embodiment, skin water loss can be expressed as a function of parameters, e.g., $$\text{Skin water loss} = f(\text{air temperature, air speed, relative humidity, temperature}_{skin}, \text{gestational age, postnatal age}) \quad \text{(Eq. 20)}.$$

For determining a body physiological parameter at block 20, one or more program 280 can determine one or more parameter referenced in Eqs. 1-20. In one embodiment for controlling a heating system at block 30 one or more program 280 can control heating system so that body core temperature remains at a setpoint. In one embodiment, one or more program 280 can control a heating system at block 30 by controlling a heating system to increase emission of heat energy in the case a current value of core temperature is determined at block 20 to be less than a setpoint and by controlling a heating system at block 30 to decrease emission of heat energy in the case a current value of core temperature is determined at block 20 to be greater than a setpoint. In one embodiment, one or more program 280 at block 30 can control a heating system using an application of one or more or Rule 1, Rule 2 or Rule 3 as follows:

Rule 1: If temperature$_{core}$<37 then warmer power level= (Net heat balance/maximum warmer power) $e^{(37-temperature\_core)/0.5}$ Rule 2: If temperature$_{core}$=37 then warmer power level= (Net heat balance/maximum warmer power)

Rule 3: If temperature$_{core}$>37 then warmer power level= (Net heat balance/maximum warmer power) $e^{(37-temperature\_core)/3}$ One or more program 280 can determine a Net heat balance as a function of Total heat loss from a body and heat gain by Metabolism, e.g., $$\text{Net heat balance (to be provided by a warmer)} = \text{Total heat loss from body} - \text{Metabolism} \quad \text{(Eq. 21)}$$

In one embodiment total heat loss from a body can be expressed as a function of parameters, e.g., $$\text{Total heat loss from body} = \text{Heat loss through respiration} + \text{Heat loss to mattress} + \text{Heat loss to air currents} + \text{Radiation heat loss} + \text{skin water loss} \quad \text{(Eq. 22)}$$

Referring to FIG. 1, one or more program 280 at block 30 can control a heating system based on a result of a determining at block 20. In one embodiment, one or more program 280 at block 30 can control a heating system to maintain a core temperature at a setpoint. In one embodiment, one or more program 280 at block 20 can determine a core temperature and at block 30 can regulate the power to a heating system to steer a core temperature to 37 C based on heat balance of the baby. The ultimate goal of apparatus 100 in one embodiment is to create a thermoneutral environment for the baby at 37 C, which means no net heat loss or gain. If a determining at block 20 indicates that a core temperature is below a setpoint, one or more program 280 at block 30 can control a heating system to increase emitted heat energy. If a determining at block 20 indicates that a core temperature is above a setpoint, one or more program 280 at block 30 can control a heating system to increase emitted heat energy. In one embodiment, a setpoint for a core temperature can be established at 37 C and one or more program 280 can control a heating system to maintain core temperature at 37 C. In one embodiment one or more program 280 can establish a setpoint for a core temperature based on or more body physiological parameter, e.g., weight, gestational age, and/or postnatal age which one or more body physiological parameter can be obtained by one or more program 280 as one or more input, e.g., one or more sensor input (e.g., weight) or one or more characterizing input (e.g., gestational age, postnatal age).

Referring to Eqs. 1-22 one or more program 280 at block 20 can perform determining of one or more body physiological parameter based on or more input. The determining at block 20 can include using one or more function as set forth in Eqs. 1-22. In one embodiment, one or more program 280 can use an input obtained by one or more program 280 as a parameter of one or more equation of Eqs. 1-22, e.g., can use an input obtained from a skin temperature sensor as a skin temperature parameter, can use an input obtained from a core temperature sensor as a core temperature parameter, can use an input obtained from a humidity sensor as a humidity parameter and so on. In one embodiment, one or more program 280 can apply a function to an obtained input to determine one or more parameter of Eqs. 1-22. For example it will be seen that the obtained inputs "baby length" "gestational age" and "postnatal age" can be subject to a function in order to determine the parameter "fraction of skin in contact with mattress" (Eq. 17) and "fraction of skin exposed to air" (Eq. 18). Where an input is capable of being measured with a sensor, a sensor can be used to measure the input. An input obtained from a sensor can be regarded as a sensor input. An input obtained from a sensor can be obtained in an online manner without operator entry of the input or can be obtained with operator entry of the input. Where an input is not measured with a sensor it can be regarded as a characterizing input that is not a sensor input. A characterizing input can be entered by an operator.

While a set of functions is provided in Eqs. 1-22 for determining set of body physiological parameters it is seen that one or more program 280 can use a reduced set of functions for determining a reduced set of body physiological parameters, e.g. one or more parameter. While a set of heat balance equations is illustrated there can be provided in an alternative embodiment a single heat balance equation or no heat balance equation. In general using reduced or otherwise simplified equations having functions with fewer parameters can be advantageous for simplified design complexity and reduced processing speed. In general using equations having functions with more parameters can be advantageous for increased accuracy and resolution. It will be understood that one or more inputs obtained for performing of determining at block 20 can change depending on particular aspects of apparatus 100. For example, where apparatus 100 is provided by a baby warmer or is of another open air form factor functions used for determining by one or more program 280 can be expected to be relatively more dependent on air temperature and air velocity.

Where apparatus 100 is provided by a baby warmer in one embodiment (e.g., as shown in FIG. 3), a top of a sidewall of an infant holding area 302 can have mounted thereon in a sensor 228 provided by an air temperature sensor (closer to foreground in FIG. 3), and a sensor 228 provided by an air velocity sensor (closer to a background in FIG. 3). Such locating of the air temperature sensor and an air velocity sensor can be selected so that sensed air temperature and velocity are representative of air temperatures and velocities to which an infant held within infant holding area 302 is exposed. Where apparatus 100 is provided by a baby warmer (e.g., as shown in FIG. 3) a heating device 240 defining a heating system is typically placed above infant holding area 302 as shown in FIG. 3 and radiant heat can be spread substantially uniformly in the vicinity of an infant using a reflector 304. Where apparatus 100 is provided by a baby warmer there may be no forced convection of heated air. The open environment provides easy access to an infant.

Where apparatus 100 is provided by an incubator (e.g., as shown in FIG. 4), each of an air temperature sensor and an air velocity sensor can be disposed internal to an enclosed infant holding area 302 in one embodiment. An incubator typically includes a closed loop heating system and a heating device 240 defining a heating system can be present anywhere within apparatus 100. Heated air can be circulated through the incubator typically using a blower (fan). Referring to functions for use in performing determining at block 20, e.g. as set forth in Eqs. 1-22 in an illustrative embodiment herein, functions used for representing a heating system can vary dependent on particular form of the heating system of apparatus 100.

For solving one or more heat balance question as set forth herein and/or one or more differential equations, one or more available software tools. In one embodiment, software tools for use in performing determining at block 20 can include software tools incorporated in one or more of the following: MAXIMA, GNU OCTAVE, GNU R, MATHEMATICA, MATLAB, COPASI, SCILAB, or MAPLE.

One or more program 280 for performance of block 20 can use one or more input. In one embodiment, the one or more input can be a one time obtained input. In one embodiment the one or more input can be a repetitively obtained input. In one embodiment, the one or more input can be a sensor input obtained from a sensor. In one embodiment, the one or more input can be a characterizing input that is not a sensor input. In one embodiment, the one or more input can be an online input, e.g., one that is automatically obtained without operator activity. In one embodiment, the one or more input can be an operator entered input obtained based on an entry of an operator. In one embodiment, the one or more input can be a physiological sensor input obtained from a physiological sensor. In one embodiment, the one or more input can be an environmental sensor input obtained from an environmental sensor. In one embodiment, one or more program 280 at block 20 for performing determining of one or more body physiological parameter can process a plurality of inputs, e.g., neonatal weight/length/age, air temperature/velocity and blood/respiratory rates.

Embodiments herein recognize that a lack of a thermal comfort model leads bedside caregivers to erroneous temperature setpoints on infant temperature control apparatus potentially contributing to increased infection, mortality, treatment costs and length of hospital stay in case of 66-93% of preterm newborns with extremely low birth weight. Embodiments herein recognize that a newborn's postnatal progress is strongly correlated to the sustenance of its core at 37+/−0.5 C. Embodiments herein recognize that commercially available apparatus for providing warming e.g., radiant warmers rely on operator judgment and single-point skin temperature measurement to attempt to achieve a stable core temperature for an infant.

In one embodiment, one or more program 280 at block 20 can determine various body physiological parameters. Referring to Table A there are summarized skin/core temperature parameters for a baby under a radiant warmer (mass 1.6 Kg, height 40 cm, room at 25 C with 0.025 m/s air flow, gestational age 32 weeks, postnatal age 1 day, tidal volume 8.5 ml/Kg, blood circulation period 60 s) under different physiological conditions. One or more program 280 at block 30 can adjust a radiant warmer's power to produce a constancy of 37 C core. Table A represents steady-state estimates for different running conditions, where steady state means the time-invariant state a baby achieve after equilibrating with the warmer and environment.

TABLE A

| Breathing freq. [/min] | Blood volume [ml/Kg] | Core temperature [C.] | Core-to skin difference [C.] |
|---|---|---|---|
| 40 | 75 | 37.0 | 2.2 |
| 80 | 75 | 37.0 | 1.6 |
| 80 | 100 | 37.0 | 1.0 |

Referring to Table A, embodiments herein recognize that core-to-skin temperature difference can have substantial variability dependent on the baby's physiological parameters and other parameters. Under a first set of conditions, a core-to-skin difference can be 1 degree C. Under a second set of conditions, a core-to-skin difference can be 2.2 degrees C. Embodiments herein recognize that regulating a heating apparatus using baby's skin temperature measurement can be inadequate and can pose risk to patients including infant patients. Embodiments herein recognize that if a core temperature of a patient is controlled to value that deviates from a target value even by a small amount a significant risk can be posed to a patient. Embodiments herein recognize that physiological parameters such as one or more of patient size, breathing frequency, or blood volume can significantly impact a thermal conductivity between a patient skin and a patient core.

Further details are set forth herein are set forth in reference to illustrative EXAMPLE 1 illustrating a specific use case with a specifically configured apparatus 100 as set forth herein.

EXAMPLE 1

Figure 5:
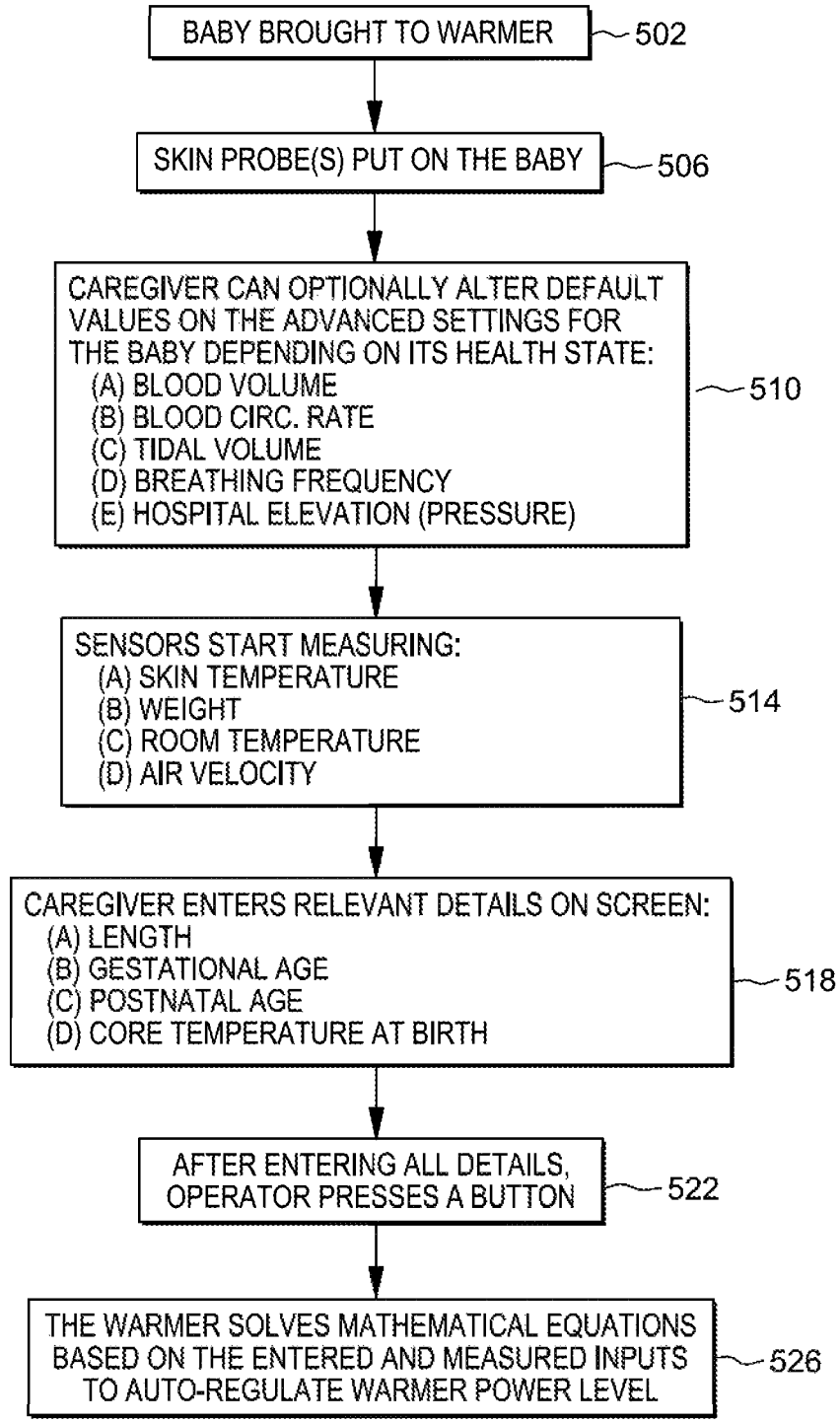
FIG. 5 is a flow diagram illustrating a method according to one embodiment.

With reference to the flow diagram of FIG. 5 provided for illustrative purposes a newborn can be brought (block 502) to an apparatus 100 provided by a baby warmer which can have the general form as shown in FIG. 3. One or more skin temperature probe (block 506) can be placed on the baby to monitor its skin temperature. Optionally, e.g., for babies with specific health conditions, the operator caregiver can alter default values on the advanced settings (at block 510), namely, (a) blood volume (b) blood circulation rate (c) tidal volume (d) breathing frequency (e) hospital elevation (atmospheric pressure). These values can be altered through a touchscreen or keypad or other user interface device 226 of apparatus 100. These operator entered values can include sensor values that can be obtained by one data or more program 280 as sensor inputs. These operator entered values can include one or more characterizing values other than sensor values that can obtained by one or more program 280 as one or more characterizing input. Contemporaneously with the data entry at block 514 one or more sensor 228 of apparatus 100 can commence providing of data for obtaining by one or more program 280 as one or more input.

Next, the operator caregiver (block 518) can key into apparatus 100 characterizing information about the baby, e.g., (i) height (ii) gestational age (iii) postnatal age which information can be obtained by apparatus 100 as characterizing inputs. An operator caregiver can also enter a most recent core temperature measurement obtained from a core temperature sensor. The operator (block 522) can then start the warmer with a single key press. Exemplary user interface screen displays 260 of apparatus 100 for entry and/or presentment of data are set forth herein with reference to FIGS. 6-8.

A warmer bed of apparatus 100 can be integrated with a sensor provided by a weight scale. A weight sensor can measure the baby weight. Apparatus 100 can be mounted with sensors provided by airflow temperature and velocity sensors that can repeatedly provide airflow temperature and velocity inputs e.g., at a configurable predetermined interval. The apparatus 100 provided by a baby warmer can also start recording the skin temperature from the probes mounted on the baby's skin.

At block 526 apparatus 100 can determine one or more body physiological parameter and can provide a control to control a heating system having one or more heating device 240 based on a result of the determining. Using the inputs from the operator caregiver and mounted sensors, a signal processing circuit 200 of apparatus 100 can solve one or more heat balance equation, e.g., three heat balance equations for the baby's core, blood and skin. It will be seen that block illustrates an implementation of blocks 20 and 30 herein in one embodiment.

Since the apparatus provided in one embodiment by a radiant warmer imposes heat radiation on the baby's skin, the heat balance equation for the skin includes a term accounting the radiant warmer heat. The heat balance equations can be solved using an objective function that regulates the power level of the warmer at a predetermined frequency to ensure constancy of the core at 37 C. This can be done in the illustrative embodiment herein by assigning the radiant warmer a power level that represents the net heat loss from the baby's body at core temperature of 37 C. At core temperatures higher than 37 C, the power level of the warmer tapers off to zero, while at core temperatures below 37 C, the warmer heat over-compensates the net heat loss. In summary, apparatus 100 can solve these equations and evolves a heating system power-level v/s time curve that is fed into the warmer heating element. The equations also provide core, blood and temperature over time curves.

For purpose of checks and balances, intermittently, the skin probe temperatures can be compared to the predicted skin temperature at that time instant. If a deviation is noticed, the equations can be re-solved by assigning the most recently measured temperatures as initial values in the math equations.

The end result of the above is the operator does not have to exercise any personal judgment. Apparatus 100 can sustain the baby's core at 37 C using the physics of heat balance.

END OF EXAMPLE 1

Additional examples and use cases are set forth in reference to FIGS. 6A- 8 E. It will be seen that one or more program 280 can perform determining of one or more physiological parameter that can provide useful controls that vary under a variety of conditions.

FIGS. 6A-6E illustrate a variety of user interface screen displays 260 of apparatus 100 in a typical use case. It is seen that an infant can be placed on an apparatus 100 with a relatively low core temperature. Then, core temperature can be increased with use of apparatus 100. It is seen that a power level control to a heating system can be at a relatively high level for a short period after an introduction of an infant to apparatus 100. Then, after a setpoint control temperature is reached, power level can be decreased.

Referring to FIGS. 6A-6C user interface screen displays 260 can display inputs obtained from sensors or from an operator and can permit overriding of such inputs by inputs obtained by an operator. The user interface screen displays of FIG. 6A-6B display inputs which can have a significant effect on patient thermal conductivity in all instances. The user interface screen display of FIG. 6C displays inputs which can have a greater effect on thermal conductivity in the case of a specialized patient having certain specialized conditions.

FIGS. 7A-7E illustrate a variety of user interface screen displays 260 of apparatus 100 in a use case in which an infant has an atypically high circulation frequency. A high circulation frequency can be expected to increase a rate at which an infant's core temperature can be increased, and can also be expected to increase a rate at which heat can be loss from a core. Accordingly, in the example of FIG. 7, a period for a core temperature reaching a setpoint can be expected to be shorter. Further, with a higher rate of heat gain at a patient's core a heating system power level for maintaining core temperature at a setpoint can be expected to be lower.

FIGS. 8A-8E illustrate a variety of user interface screen displays 260 of apparatus 100 in a use case in which there are quiescent room conditions (generally characterized by stable air temperature and air velocity). In such a use case, one or more program 280 can control a heating system to low power level that is relatively constant over time, and the infant's core can be warmed to setpoint within a reasonable period with a relatively low power heating system control.

Referring to the user interface screen displays of FIGS. 6D and 6E, 7D and 7E, and 8E and 8D user interface screen displays can display determined parameters wherein the determined parameters are provided by determined function that vary over time. In one embodiment, as indicated by Eq. 1 Eq. 2 and Eq. 3 one or more program 280 can solve time derivative differential equations and accordingly can determine one or more patient physiological parameter as a time varying function having a value that varies over time.

In one embodiment, one or more program 280 can repetitively and continuously obtain one or more sensor input from a sensor and can perform patient physiologically parameter determining in a manner so that a control for controlling a heating system at block 30 is based on a current input obtained from one or more sensor.

However, because one or more program 280 can determine time variable functions for a certain parameter, a current value for one or more parameter determined by one or more program 280 can be a projected value determined using a previously determined time variable function. In one embodiment, the previously determined time variable function determined by one or more program 280 can be determined based on a prior obtained one or more input, and a current value for one or more parameter determined by one or more program 280 can be determined based on one or more prior obtained input.

In one embodiment, one or more program 280 for parameter determining does not repetitively continuously obtain one or more sensor output for performing parameter determining for heat system control, but rather can rely e.g., during a majority of periods of operation on a prior determined time varying function for one or more parameter, and can perform obtaining of one or more sensor output for controlling a heating system on a basis other than repetitively continuously, e.g., at one or more time of an event such an alarm condition event or a baby loading event as set forth herein, or at scheduled read operation times, e.g., on a once per hour, once every two hours, once every five hours, or once per day basis.

In one embodiment, where one or more program 280 controls a heating system based on prior determined time varying parameter functions, a current time T0 in the screen displays of FIGS. 6D-6E can be represented as the time "0" such that the times "1 Hour" and "2 Hours" show projections of the represented determined time varying parameter values at future times, where the projections are performed using one or more previously determined time variable function. In one embodiment, time "0" of FIGS. 6D and 6E the data of FIGS. 6D and 6E can be continuously updated so that current values are represented at time "0" with data associated to times to the right of time "0" representing future projections based on previously determined time varying functions for one or more parameter.

In one embodiment, one or more program 280 can determine an alarm condition and can perform obtaining of one or more sensor output to determine one or more parameter for controlling a heating system, e.g., prior to a scheduled sensor read operation, responsively to an alarm condition being satisfied.

In one embodiment, one or more program 280 can determine that an alarm condition is satisfied when an input from one or more sensor satisfies a predetermined criteria, e.g., changes by more than a threshold change rate, deviates from a prior value by more than a threshold value, or deviates from a predetermined value by more than a threshold value, or deviates from a projected value by more than a threshold value.

Embodiments herein recognize that inputs of certain sensors e.g., air temperature sensor an air velocity sensor, can have a significant impact on determined body physiological parameter values. Accordingly, in one embodiment, one or more program 280 can determine that an alarm condition is satisfied based on an input obtained from an air temperature sensor. In one embodiment, one or more program 280 can determine that an alarm condition has been satisfied when an air temperature sensor satisfies a predetermined criteria, e.g., changes by more than a threshold change rate, deviates from a prior value by more than a threshold value, or deviates from a predetermined value by more than a threshold value, or deviates from a projected value by more than a threshold value. In one embodiment, one or more program 280 can determine that an alarm condition is satisfied based on an input obtained from an air velocity sensor. In one embodiment, one or more program 280 can determine that an alarm condition has been satisfied when an air velocity sensor satisfies a predetermined criteria, e.g., changes by more than a threshold change rate, deviates from a prior value by more than a threshold value, or deviates from a predetermined value by more than a threshold value, or deviates from a projected value by more than a threshold value.

In one embodiment, one or more program 280 can determine that an alarm condition is satisfied when a sensor measured value for a parameter deviates from its projected value by a threshold amount. For example, one or more program 280 can be using as a current value for skin temperature a value based on a prior determined time varying function and one or more program 280 can be monitoring an output obtained from a skin temperature sensor. One or more program 280 when there is a threshold exceeding difference between the values can determine that an alarm condition is present.

In one embodiment, one or more program 280 can perform a location optimization function to determine an optimum location of apparatus 100 within an environment. Referring to FIGS. 6D, 7D, and 8D, it is seen that a power level control profile for a heating system of apparatus 100 can change depending on sensed conditions. While there are different patient conditions in the examples of FIGS. 6D, 7D and 8D, it will be seen that a power level control profile can change based on environmental conditions irrespective of patient conditions. In one embodiment, one or more program can be operative to (a) display prompts that prompt an operator to move apparatus 100 to various locations in an environment. One or more program 280 can be further operative so that (b) at each new location one or more program determines a power level profile projections of the type indicated in FIGS. 6D, 7D and 8D. One or more program 280 can be further operative to determine the best location out of the plurality locations and to output a prompt prompting the user to locate the apparatus 100 at the determined best location. One or more program 280 can determine the best location based on a predetermined criteria, e.g., the lowest overall power consumption, or the flattest power level profile, comfort to a patient (which can be provided by a flatter power level profile). In some applications a flat power level profile, with relatively flat increases and/or decreases in power level can be determined to pose least risk to a patient.

In one embodiment, one or more program 280 can incorporate a safety feature so that control of a heating system is performed in a manner that addresses safety of a patient being warmed. Embodiments herein recognize that if a patient is warmed too quickly a health of a patient might be compromised. In one embodiment, a heating system of apparatus 100 can be capable of providing a maximum warming rate and can be controlled in a manner to provide warming at a rate less than a maximum warming rate. In one embodiment, a heating system can be capable of providing a maximum warming rate by being rated for providing the maximum warming rate. In one embodiment for providing such safe warming control a heating system can include a maximum power level and can be controlled to emit heat at less than the maximum power level. Referring to one embodiment, it will be seen that Rules 1, 2, and 3 herein have features so that heating system can be controlled in a manner to provide warming to a patient at less than a maximum heating rate. Embodiments herein recognize that if a patient is cooled too quickly a health of a patient might be compromised. In one embodiment, a heating system of apparatus 100 can be capable of providing a maximum cooling rate and can be controlled in a manner to provide cooling at a rate less than a maximum cooling rate. In one embodiment for providing such safe cooling control a heating system can include a minimum power level (e.g., power shut off) and can be controlled to emit heat at greater than the minimal power level. For example, a heating system can be controlled to provide more than the minimal amount of heat that would be provided via a full power shut off. Referring to one embodiment, it will be seen that Rules 1, 2, and 3 herein have features so that heating system can be controlled in a manner to provide cooling to a patient at rate less than a maximum cooling rate.

Embodiments herein allow a patient warming heating system to be controlled in a manner that is substantially non-invasive to a patient. In one embodiment apparatus 100 can optionally include a sensor applied to a patient e.g. a skin temperature sensor, but need not rely on such sensor for determining a current body physiological parameter including a current body temperature parameter. In one embodiment, apparatus 100 can be absent of any body contacting sensor such as any body core temperature sensor or skin temperature sensor. In one embodiment, apparatus 100 does not rely on a current input from any body contacting temperature sensor for determining a current body temperature parameters, e.g., core, blood or skin temperature parameter.

For providing heating system control that is substantially non-invasive, methods and apparatus herein in one aspect can determine one or more body temperature parameter based on, e.g., using, one or more input other than an input from a body contacting temperature sensor, e.g. one or more input from an environmental sensor and/or one or more input in the form of characterizing data that is not a sensor obtained input as set forth herein.

For providing heating system control that is substantially non-invasive, methods and apparatus herein in one aspect can determine one or more body temperature parameter based on one or more input from a body temperature sensor disposed at a body location spaced apart from a location for which body temperature parameter is being determined. In one example, one or more program 280 performing determining at block 20 can perform determining of a body core temperature parameter based on an input obtained from a skin temperature sensor. In one example, one or more program 280 performing determining at block 20 can perform determining of a body blood temperature parameter based on an input obtained from a skin temperature sensor. In one example, one or more program 280 performing determining at block 20 can perform determining of a body skin temperature parameter based on an input obtained from a body core temperature sensor (e.g., a rectal thermometer).

By basing determining at block 20 on one or more input in various embodiments as set forth herein one or more program 280 can increase an accuracy of a determining.

For providing heating system control that is substantially non-invasive, methods and apparatus herein in one aspect can perform determining at block 20 by determining a time varying function for one or more body physiological parameter. As set forth herein one or more program 280 can solve one or more differential equation to determine one or more time varying function for, e.g., core temperature, blood temperature, and/or skin temperature. By determining one or more time varying function for one or more body physiological parameter, methods and apparatus herein can perform determining of one or more current body physiological parameter without reliance on an obtaining of any current input from a sensor such as a body contacting temperature sensor.

There is set forth herein in one embodiment a method comprising determining at block 20 (FIG. 1) one or more body physiological parameter of a patient based on one or more input; and controlling at block 30 a heating system for warming the patient based on a result of the determining. In one embodiment the one or more body physiological parameter can include a body temperature parameter selected from the group consisting of a body core temperature, a blood temperature and a skin temperature.

In one embodiment, the determining at block 20 can include performing the determining based on one or more input other than an input obtained from a body contacting temperature sensor, e.g., characterizing data as set forth herein and/or one or more input obtained from an environmental sensor. In one embodiment the one or more body physiological parameter can include one or more body temperature parameter and the determining at block 20 can include determining the one or more body temperature parameter based on one or more input other than an input obtained from a body contacting temperature sensor.

In one embodiment, the determining at block 20 can include determining one or more body physiological parameter provided by an internal body temperature parameter such as a body core temperature and/or a blood temperature.

In one embodiment, the one or more input at block 20 can include at least one prior obtained input. For example, as set forth herein, one or more program 280 for performing determining at block 20 can determine a current value for a body physiological parameter using a prior determined time varying function for the body physiological parameter, wherein one or more program, 280 can determine the time varying function using a prior obtained input. One or more program 280 can determine a time varying function at block 20 in one embodiment by solving one or more heat balance differential equation.

Where one or more input at block 20 includes a prior obtained input, the prior obtained input can be, e.g., an input obtained an appreciable time before a current time. An appreciable time before a current time can be, e.g., in one embodiment, a time longer than a processing latency delay. An appreciable time before a current time in one embodiment can be, e.g., a time longer than a threshold time, e.g., longer that 10 seconds in one embodiment, longer that 30 seconds in one embodiment, longer than 1 minute in one embodiment, longer than 10 minutes in one embodiment, longer than 30 minutes in one embodiment, longer than 1 hour in one embodiment, longer than 3 hours in one embodiment, longer than 10 hours in one embodiment, longer than one day in one embodiment.

In one embodiment, the one or more input at block 20 can include a prior obtained temperature measurement, a prior obtained air temperature and a prior obtained air velocity. In one embodiment, as has been set forth herein, the determining at block 20 can include determining a current value for an internal body temperature parameter using a prior obtained one or more input by determining a time varying function for the one or more internal body temperature parameter and using the time varying function.

A small sample of apparatus, methods and systems set forth herein include the following:

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an apparatus including: an infant holding area. The apparatus also includes a heating system for warming the infant holding area. The apparatus also includes where the apparatus is operative for determining one or more body physiological parameter of an infant based on a plurality of inputs, and for controlling the heating system based on result of the determining, where the plurality of inputs includes a first input and a second input. Other embodiments of this aspect include corresponding computer systems, apparatus, and computer programs recorded on one or more computer storage devices, each configured to perform the actions of the methods.

Implementations may include one or more of the following features. The apparatus where the one or more body physiological parameter includes a body temperature parameter selected from the group consisting of a body core temperature, a blood temperature and a skin temperature. The apparatus where the first input is an input other than an input obtained from a body contacting temperature sensor. The apparatus where the first input is an input obtained from a weight sensor. The apparatus where the first input is an input obtained from a temperature sensor and the second input is an input obtained from a weight sensor. The apparatus where the one or more body physiological parameter includes an internal body temperature parameter. The apparatus where the one or more body physiological parameter includes a body core temperature parameter. The apparatus where the plurality of inputs include as the first input a prior obtained temperature measurement, as the second input a prior obtained air temperature and a prior obtained air velocity, and where the one or more body physiological parameter is a current body physiological parameter. The apparatus where the first input is a prior obtained input, and where the determining includes determining a current value for one or more an internal body temperature parameter based on the first input. The apparatus where the first input is a prior obtained input, where the determining includes determining a current value for an internal body temperature parameter based on the first input, where the determining includes determining a time varying function for the one or more internal body temperature parameter and determining the current value for an internal body temperature parameter using the time varying function. The apparatus where the determining includes determining a time varying function for the one or more body physiological parameter. The apparatus where the determining includes using one or more heat balance equation. The apparatus where the one or more body physiological parameter includes a body core temperature, and where the controlling includes controlling the heating system to maintain the body core temperature at a setpoint. The apparatus where the one or more body physiological parameter includes a body core temperature, and where the controlling includes controlling the heating system to maintain the body core temperature at a setpoint, where apparatus is operative to establish the setpoint base d on one or more input. The apparatus where the first input is a sensor input obtained from a sensor and where the second input is a characterizing input that is not an input obtained from a sensor. The apparatus where the first input is an input obtained from a physiological sensor and the second input is an input obtained from an environmental sensor. The method where the first input is a one time obtained input and the second input is a repetitively obtained input. The method where the first input is selected from the group consisting of an input from an air temperature sensor, an input from an air velocity sensor, an input from a weight sensor, an input from a skin temperature sensor, and where the second input is selected from the group consisting of an input from a body core temperature sensor, a patient length, a patient gestational age, and a patient postnatal age. The method where the first input is selected from the group consisting of an input from an air temperature sensor and an input from an air velocity sensor, and where the second input is selected from the group consisting of an input from a skin temperature sensor and an input from a body core temperature sensor. The method where the first input is selected from the group consisting of elevation above sea level, tidal volume, breathing rate, total blood content and circulation period, and where the second input is selected from the group consisting of an input from an air temperature sensor, an input from an air velocity sensor, an input from a weight sensor, an input from a skin temperature sensor, an input from a body core temperature sensor, a patient length, a patient gestational age, and a patient postnatal age. The method where the apparatus is operative for adjusting the determining responsively to an alarm condition being satisfied. The method where the apparatus is operative for adjusting the determining responsively to an alarm condition being satisfied, where the alarm condition being satisfied is based on an input obtained from a sensor, where the sensor is selected from the group consisting of an air temperature sensor, an air velocity sensor, and a skin temperature sensor. The apparatus where the one or more body physiological parameter includes a body temperature parameter selected from the group consisting of a body core temperature, a blood temperature and a skin temperature. The apparatus where the one or more input includes at least one input that is other than an input obtained from a body contacting temperature sensor. The apparatus where the at least one prior obtained input includes a prior obtained input selected from the group consisting of (a) a prior obtained input from the skin temperature sensor (b) a prior obtained input from of core temperature sensor, and (c) a prior obtained characterizing input that is not a sensor input. The apparatus where the one or more body physiological parameter includes one or more body temperature parameter and where the determining includes determining the one or more body temperature parameter based on one or more input other than an input obtained from a body contacting temperature sensor. The apparatus where the one or more input includes an input obtained from a weight sensor. The apparatus where the determining includes determining a current value for an internal body temperature parameter based on the at least one prior obtained input, where the determining includes determining a time varying function for the one or more internal body temperature parameter and determining the current value for an internal body temperature parameter using the time varying function. The apparatus where the determining includes using one or more heat balance equation. The apparatus where the one or more body physiological parameter includes a body core temperature, and where the controlling includes controlling the heating system to maintain the body core temperature at a setpoint. The method where the first input is an input obtained from a body contacting temperature sensor, and where the second input is an input other than an input obtained from a body contacting temperature sensor. The method where the first input is an input obtained from a physiological sensor, and where the second input is obtained from an environmental sensor. The method where the first input is a sensor input, and where the second input is a characterizing input that is not a sensor input. The apparatus where the process for determining includes determining a power level profile of the apparatus at each of several locations and determining a best power level profile.

One general aspect includes an apparatus including: an infant holding area. The apparatus also includes a heating system for warming the infant holding area. The apparatus also includes where the apparatus is operative for determining a current value for one or more body physiological parameter of an infant based on one or more input, and for controlling the heating system based on result of the determining, where the one or more input includes at least one prior obtained input. Other embodiments of this aspect include corresponding computer systems, apparatus, and computer programs recorded on one or more computer storage devices, each configured to perform the actions of the methods.

Implementations may include one or more of the following features. The apparatus where the one or more body physiological parameter includes a body temperature parameter selected from the group consisting of a body core temperature, a blood temperature and a skin temperature. The apparatus where the one or more input includes at least one input that is other than an input obtained from a body contacting temperature sensor. The apparatus where the at least one prior obtained input includes a prior obtained input selected from the group consisting of (a) a prior obtained input from the skin temperature sensor (b) a prior obtained input from of core temperature sensor, and (c) a prior obtained characterizing input that is not a sensor input. The apparatus where the one or more body physiological parameter includes one or more body temperature parameter and where the determining includes determining the one or more body temperature parameter based on one or more input other than an input obtained from a body contacting temperature sensor. The apparatus where the one or more input includes an input obtained from a weight sensor. The apparatus where the determining includes determining a current value for an internal body temperature parameter based on the at least one prior obtained input, where the determining includes determining a time varying function for the one or more internal body temperature parameter and determining the current value for an internal body temperature parameter using the time varying function. The apparatus where the determining includes using one or more heat balance equation. The apparatus where the one or more body physiological parameter includes a body core temperature, and where the controlling includes controlling the heating system to maintain the body core temperature at a setpoint. The method where the first input is an input obtained from a body contacting temperature sensor, and where the second input is an input other than an input obtained from a body contacting temperature sensor. The method where the first input is an input obtained from a physiological sensor, and where the second input is obtained from an environmental sensor. The method where the first input is a sensor input, and where the second input is a characterizing input that is not a sensor input. The apparatus where the process for determining includes determining a power level profile of the apparatus at each of several locations and determining a best power level profile. Implementations of the described techniques may include hardware, a method or process, or computer software on a computer-accessible medium.

One general aspect includes a method including: determining one or more body physiological parameter of a patient based on a plurality of inputs, where the plurality of inputs include a first input and a second input. The method also includes controlling a heating system for warming the patient based on a result of the determining. Other embodiments of this aspect include corresponding computer systems, apparatus, and computer programs recorded on one or more computer storage devices, each configured to perform the actions of the methods.

Implementations may include one or more of the following features. The method where the first input is an input obtained from a body contacting temperature sensor, and where the second input is an input other than an input obtained from a body contacting temperature sensor. The method where the first input is an input obtained from a physiological sensor, and where the second input is obtained from an environmental sensor. The method where the first input is a sensor input, and where the second input is a characterizing input that is not a sensor input. The apparatus where the process for determining includes determining a power level profile of the apparatus at each of several locations and determining a best power level profile.

One general aspect includes an apparatus including: an infant holding area. The apparatus also includes a heating system for warming the infant holding area. The apparatus also includes where the apparatus is operative to perform a process for controlling the heating system to warm the infant. The apparatus also includes where the apparatus is operative to perform a process for determining a preferred location of the apparatus within an environment. Other embodiments of this aspect include corresponding computer systems, apparatus, and computer programs recorded on one or more computer storage devices, each configured to perform the actions of the methods.

Implementations may include one or more of the following features. The apparatus where the process for determining includes determining a power level profile of the apparatus at each of several locations and determining a best power level profile.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes an apparatus including: an infant holding area; a heating system for warming the infant holding area; where the apparatus is operative for determining one or more body physiological parameter of an infant based on one or more input, and for controlling the heating system based on result of the determining. Other embodiments of this aspect include corresponding computer systems, apparatus, and computer programs recorded on one or more computer storage devices, each configured to perform the actions of the methods.

Implementations may include one or more of the following features. The apparatus where the one or more body physiological parameter includes a body temperature parameter selected from the group consisting of a body core temperature, a blood temperature and a skin temperature. The apparatus where the determining includes performing the determining based on one or more input other than an input obtained from a body contacting temperature sensor. The apparatus where the one or more body physiological parameter includes one or more body temperature parameter and where the determining includes determining the one or more body temperature parameter based on one or more input other than an input obtained from a body contacting temperature sensor. The apparatus where the one or more input includes an input obtained from a weight sensor. The apparatus where the one or more input includes an input obtained from a temperature sensor and an input obtained from a weight sensor. The apparatus where the one or more body physiological parameter includes an internal body temperature parameter. The apparatus where the one or more body physiological parameter includes a body core temperature parameter. The apparatus where the one or more body physiological parameter includes an internal body temperature parameter selected from the group consisting of a body core temperature, a blood temperature. The apparatus where the one or more input includes a prior obtained temperature measurement, a prior obtained air temperature and a prior obtained air velocity, and where the one or more body physiological parameter is a current body physiological parameter. The apparatus where the determining includes determining a current value for one or more an internal body temperature parameter using a prior obtained one or more input. The apparatus where the determining includes determining a current value for an internal body temperature parameter using a prior obtained one or more input by determining a time varying function for the one or more internal body temperature parameter and using the time varying function. The apparatus where the determining includes determining a time varying function for the one or more body physiological parameter. The apparatus where the determining includes determining a current body core temperature parameter absent obtaining of a current input of a body core temperature sensor. The apparatus where the determining includes using one or more heat balance equation. The apparatus where the one or more body physiological parameter includes a body core temperature, and where the controlling includes controlling the heating system to maintain the body core temperature at a setpoint. The apparatus where the one or more input is selected from the group consisting of a sensor input and a characterizing input that is not a sensor input. The apparatus where the one or more input is selected from the group consisting of a physiological sensor input and an environmental sensor input. The method where the one or more input is selected from the group consisting of a one time obtained input and a repetitively obtained input. The method where the one or more physiological parameter includes a body temperature parameter selected from the group consisting of a body core temperature, a blood temperature and a skin temperature. The method where the determining includes performing the determining based on one or more input other than an input obtained from a body contacting temperature sensor. The method where the one or more body physiological parameter includes one or more body temperature parameter and where the determining includes determining the one or more body temperature parameter based on one or more input other than an input obtained from a body contacting temperature sensor. The method where the one or more body physiological parameter includes an internal body temperature parameter. The method where the one or more body physiological parameter includes a body core temperature parameter. The method where the one or more body physiological parameter includes an internal body temperature parameter selected from the group consisting of a body core temperature, a blood temperature. The method where the one or more input includes a prior obtained temperature measurement, a prior obtained air temperature and a prior obtained air velocity, and where the one or more body physiological parameter is a current body physiological parameter. The method where the determining includes determining a current value for one or more an internal body temperature parameter using a prior obtained one or more input. The method where the determining includes determining a current value for an internal body temperature parameter using a prior obtained one or more input by determining a time varying function for the one or more internal body temperature parameter and using the time varying function. The method where the determining includes determining a time varying function for the one or more body physiological parameter. The method where the determining includes determining a current body core temperature parameter absent obtaining of a current input of a body core temperature sensor. The method where the determining includes using one or more heat balance equation. The method where the one or more body physiological parameter is a body core temperature, and where the controlling includes controlling the heating system to maintain the body core temperature at a setpoint. The method where the one or more input is selected from the group consisting of a one time obtained input and a repetitively obtained input. The method where the one or more input is selected from the group consisting of a sensor input and a characterizing input that is not a sensor input. The method where the one or more input is selected from the group consisting of an online input and an operator entered input. The method where the one or more input is selected from the group consisting of a physiological sensor input and an environmental sensor input. The apparatus where the alarm condition being satisfied is based on an input obtained from a sensor. The apparatus where the alarm condition being satisfied is based on an input obtained from a sensor, where the sensor is selected from the group consisting of an air temperature sensor, an air velocity sensor, and a skin temperature sensor. The apparatus where the heating system is capable of providing cooling at a maximum cooling rate and where the apparatus is operative so that the heating system provides cooling to the infant at a cooling rate of less than the maximum cooling rate. Implementations of the described techniques may include hardware, a method or process, or computer software on a computer-accessible medium.

One general aspect includes a method including: determining one or more body physiological parameter of a patient based on one or more input, and controlling a heating system for warming the patient based on a result of the determining. Other embodiments of this aspect include corresponding computer systems, apparatus, and computer programs recorded on one or more computer storage devices, each configured to perform the actions of the methods.

Implementations may include one or more of the following features. The method where the one or more physiological parameter includes a body temperature parameter selected from the group consisting of a body core temperature, a blood temperature and a skin temperature. The method where the determining includes performing the determining based on one or more input other than an input obtained from a body contacting temperature sensor. The method where the one or more body physiological parameter includes one or more body temperature parameter and where the determining includes determining the one or more body temperature parameter based on one or more input other than an input obtained from a body contacting temperature sensor. The method where the one or more body physiological parameter includes an internal body temperature parameter. The method where the one or more body physiological parameter includes a body core temperature parameter. The method where the one or more body physiological parameter includes an internal body temperature parameter selected from the group consisting of a body core temperature and a blood temperature. The method where the one or more input includes a prior obtained temperature measurement, a prior obtained air temperature and a prior obtained air velocity, and where the one or more body physiological parameter is a current body physiological parameter. The method where the determining includes determining a current value for one or more an internal body temperature parameter using a prior obtained one or more input. The method where the determining includes determining a current value for an internal body temperature parameter using a prior obtained one or more input by determining a time varying function for the one or more internal body temperature parameter and using the time varying function. The method where the determining includes determining a time varying function for the one or more body physiological parameter. The method where the determining includes determining a current body core temperature parameter absent obtaining of a current input of a body core temperature sensor. The method where the determining includes using one or more heat balance equation. The method where the one or more body physiological parameter is a body core temperature, and where the controlling includes controlling the heating system to maintain the body core temperature at a setpoint. The method where the one or more input is selected from the group consisting of a one time obtained input and a repetitively obtained input. The method where the one or more input is selected from the group consisting of a sensor input and a characterizing input that is not a sensor input. The method where the one or more input is selected from the group consisting of an online input and an operator entered input. The method where the one or more input is selected from the group consisting of a physiological sensor input and an environmental sensor input. The apparatus where the alarm condition being satisfied is based on an input obtained from a sensor. The apparatus where the alarm condition being satisfied is based on an input obtained from a sensor, where the sensor is selected from the group consisting of an air temperature sensor, an air velocity sensor, and a skin temperature sensor. The apparatus where the heating system is capable of providing cooling at a maximum cooling rate and where the apparatus is operative so that the heating system provides cooling to the infant at a cooling rate of less than the maximum cooling rate. Implementations of the described techniques may include hardware, a method or process, or computer software on a computer-accessible medium.

One general aspect includes an apparatus including: an infant holding area, a heating system for warming the infant holding area, where the apparatus is operative to perform a process for controlling the heating system to warm the infant, and where the apparatus is operative to adjust the process for controlling responsive to an alarm condition being satisfied. Other embodiments of this aspect include corresponding computer systems, apparatus, and computer programs recorded on one or more computer storage devices, each configured to perform the actions of the methods.

Implementations may include one or more of the following features. The apparatus where the alarm condition being satisfied is based on an input obtained from a sensor. The apparatus where the alarm condition being satisfied is based on an input obtained from a sensor, where the sensor is selected from the group consisting of an air temperature sensor, an air velocity sensor, and a skin temperature sensor. The apparatus where the heating system is capable of providing cooling at a maximum cooling rate and where the apparatus is operative so that the heating system provides cooling to the infant at a cooling rate of less than the maximum cooling rate. Implementations of the described techniques may include hardware, a method or process, or computer software on a computer-accessible medium.

One general aspect includes an apparatus including: an infant holding area, a heating system for warming the infant holding area, where the heating system is capable of warming an infant at a maximum warming rate, and where the apparatus is operative to control the heating system so that the heating system provides warming to the infant at a warming rate less than the maximum warming rate. Other embodiments of this aspect include corresponding computer systems, apparatus, and computer programs recorded on one or more computer storage devices, each configured to perform the actions of the methods.

Implementations may include one or more of the following features. The apparatus where the heating system is capable of providing cooling at a maximum cooling rate and where the apparatus is operative so that the heating system provides cooling to the infant at a cooling rate of less than the maximum cooling rate. Implementations of the described techniques may include hardware, a method or process, or computer software on a computer-accessible medium.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Forms of term "based on" herein encompass relationships where an element is partially based on as well as relationships where an element is entirely based on. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure. It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments. Accordingly, the invention is not to be seen as limited by the foregoing description, but is only limited by the scope of the appended claims.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A medical apparatus for neonatal warming comprising:
   an infant holding area of at least one of an incubator and a baby warmer;
   a heating system of at least one of the incubator and the baby warmer configured to warm the infant holding area;
   wherein the apparatus is configured to determine a current value for one or more body physiological parameter(s) of an infant based on a plurality of inputs, and to control the heating system based on the determined current body physiological parameter(s);
   wherein the plurality of inputs includes a prior obtained body temperature measurement, a prior obtained air temperature, and a prior obtained air velocity; and
   wherein the current value for the one or more body physiological parameter(s) is determined based on a time varying function for the prior obtained body temperature measurement, the prior obtained air temperature, and the prior obtained air velocity.

2. The apparatus of claim 1, wherein the one or more body physiological parameter(s) includes a body temperature parameter selected from the group consisting of a body core temperature, a blood temperature and a skin temperature.

3. The apparatus of claim 1, wherein the plurality of inputs further includes an input obtained from a weight sensor.

4. The apparatus of claim 1, wherein the one or more body physiological parameter(s) includes an internal body temperature parameter.

5. The apparatus of claim 1, wherein the apparatus is configured to determine the current value for one or more body physiological parameter(s) by determining a time varying function for an internal body temperature parameter and determining a current value for the internal body temperature parameter using the time varying function for the internal body temperature parameter.

6. The apparatus of claim 1, wherein the apparatus is configured to determine the current value for one or more body physiological parameter(s) using one or more heat balance equation(s).

7. The apparatus of claim 1, wherein the one or more body physiological parameter(s) includes a body core temperature, and wherein the apparatus is configured to control the heating system to maintain the body core temperature at a setpoint.

8. The apparatus of claim 1, wherein the one or more body physiological parameter(s) includes a body core temperature;
   wherein the apparatus is configured to control the heating system to maintain the body core temperature at a setpoint; and wherein the apparatus is operative to establish the setpoint based on at least one input of the plurality of inputs.

9. The apparatus of claim 1, wherein the plurality of inputs further includes a characterizing input that is not an input obtained from a sensor.

10. The apparatus of claim 1, wherein the plurality of inputs includes an input obtained from a physiological sensor and an input obtained from an environmental sensor.

11. The apparatus of claim 1, wherein the plurality of inputs further includes at least one of an input from a weight sensor, an input from a skin temperature sensor, an input from a body core temperature sensor, a patient length, a patient gestational age, and a patient postnatal age.

12. The apparatus of claim 1, wherein the plurality of inputs further includes elevation above sea level, tidal volume, breathing rate, total blood content and circulation period, an input from a weight sensor, an input from a skin temperature sensor, an input from a body core temperature sensor, a patient length, a patient gestational age, and a patient postnatal age.

13. The apparatus of claim 1, wherein the apparatus is operative to adjust the current value for the one or more body physiological parameter(s) responsively to an alarm condition being satisfied.

14. The apparatus of claim 1, wherein the apparatus is operative for adjusting the determining responsively to an alarm condition being satisfied, wherein the alarm condition being satisfied is based on an input obtained from a sensor, wherein the sensor is selected from the group consisting of an air temperature sensor, an air velocity sensor, and a skin temperature sensor.

15. The apparatus of claim 1, wherein the prior obtained body temperature measurement is at least one of a body core temperature measurement, a blood temperature measurement and a skin temperature measurement.

16. A medical apparatus for neonatal warming comprising:
- an infant holding area of at least one of an incubator and a baby warmer;
- a heating system of at least one of the incubator and the baby warmer configured to warm the infant holding area;
- wherein the apparatus is configured to determine a current value for one or more body physiological parameter(s) of an infant based on prior obtained inputs, including at least a prior obtained body temperature measurement, a prior obtained air temperature, and a prior obtained air velocity, and a time varying function for the prior obtained inputs; and
- wherein the apparatus is configured to control the heating system based on the determined current value for the one or more body physiological parameter(s).

17. The apparatus of claim 16, wherein the one or more body physiological parameter(s) includes a body temperature parameter selected from the group consisting of a body core temperature, a blood temperature and a skin temperature.

18. The apparatus of claim 16, wherein the one or more body physiological parameter(s) is further based on at least one input that is other than an input obtained from a body contacting temperature sensor.

19. The apparatus of claim 16, wherein the prior obtained inputs further includes a prior obtained input selected from the group consisting of (a) a prior obtained input from a skin temperature sensor, (b) a prior obtained input from a core temperature sensor, and (c) a prior obtained characterizing input that is not a sensor input.

20. The apparatus of claim 16, wherein the one or more body physiological parameter(s) includes one or more body temperature parameter(s); and
- wherein the apparatus is configured to determine the current value for one or more body physiological parameter(s) by determining the one or more body temperature parameter(s) based on one or more input(s) other than an input obtained from a body contacting temperature sensor.

21. The apparatus of claim 16, wherein the one or more body physiological parameter(s) is further based on an input obtained from a weight sensor.

22. The apparatus of claim 16, wherein the apparatus is configured to determine the current value for one or more body physiological parameter(s) by determining a time varying function for an internal body temperature parameter based on the prior obtained inputs and determining a current value for the internal body temperature parameter using the time varying function for the internal body temperature parameter.

23. The apparatus of claim 16, wherein the apparatus is configured to determine the current value for one or more body physiological parameter(s) using one or more heat balance equation(s).

24. The apparatus of claim 16, wherein the one or more body physiological parameter(s) includes a body core temperature, and wherein the apparatus is configured to control the heating system to maintain the body core temperature at a set point.

25. A method for neonatal warming comprising:
- determining a current value for one or more body physiological parameter(s) of a patient based on a plurality of inputs, wherein the plurality of inputs include at least a prior obtained body temperature measurement, a prior obtained air temperature, and a prior obtained air velocity, and wherein the determining includes determining a current value for the one or more body physiological parameter(s) based on a time varying function for the prior obtained body temperature measurement, the prior obtained air temperature, and the prior obtained air velocity;
- controlling a heating system of at least one of an incubator and a baby warmer to warm the patient based on a result of the determining; and
- wherein controlling the heating system comprises:
- determining a power level profile based on a power consumption to maintain the one or more body physiological parameter(s) of the patient at each of several locations within an environment; and
- determining, based on the power level profile, a preferred location of the at least one of the incubator and the baby warmer within the environment for controlling the heating system to maintain the one or more body physiological parameter(s) of the infant.

26. The method of claim 24, wherein the plurality of inputs include at least one input obtained from a physiological sensor and at least one input is obtained from an environmental sensor.

27. The method of claim 24, wherein the plurality of inputs include at least one a sensor input and at least one characterizing input that is not a sensor input.

28. A medical apparatus for neonatal warming comprising:
- an infant holding area configured to hold an infant;
- a heating system for warming the infant holding area;
- wherein the apparatus is operative to perform a process for controlling the heating system to maintain a body physiological parameter of the infant; and
- wherein the apparatus is configured to determine a power level profile based on a power consumption to maintain the body physiological parameter of the infant at each of several locations within an environment and to determine, based on the power level profile, a preferred location of the apparatus within the environment for controlling the heating system to maintain the body physiological parameter of the infant.

29. The apparatus of claim 28, wherein the apparatus is further configured to determine an overall power consumption and/or an overall power level profile for the environment based on the power level profile at each of the several locations.

30. The apparatus of claim 28, wherein the preferred location of the apparatus within the environment is based on a predetermined prior obtained power level criteria, including at least one of a lowest overall power consumption and a flattest power level profile.

* * * * *